United States Patent
Allen et al.

(10) Patent No.: US 6,651,520 B1
(45) Date of Patent: Nov. 25, 2003

(54) INTERFACE BETWEEN A PIECE OF BAGGAGE AND A PRECONCENTRATOR

(75) Inventors: William C. Allen, Colorado Springs, CO (US); Leighton Ige, Honolulu, HI (US)

(73) Assignee: Preventure Security Solutions, Inc., Charlestown, MA (US)

( * ) Notice: Subject to any disclaimer, the term of this patent is extended or adjusted under 35 U.S.C. 154(b) by 0 days.

(21) Appl. No.: 10/224,719

(22) Filed: Aug. 21, 2002

(51) Int. Cl.[7] .............................................. B65D 81/20
(52) U.S. Cl. ................. 73/863.81; 206/529.8; 137/512.15; 73/64.56
(58) Field of Search .................... 73/863.81, 863.83, 73/863.85, 64.56, 23, 23.2, 23.6; 215/228, 262; 220/212, 231, 240; 206/829, 543; 190/119, 109, 110, 102, 120, 36; 55/261, 266, 270, 355, 460, 476; 403/24

(56) References Cited

U.S. PATENT DOCUMENTS

| | | | |
|---|---|---|---|
| 3,699,333 A | | 10/1972 | Cohen et al. ................ 250/282 |
| 4,002,081 A | * | 1/1977 | Schultz, Jr. .................. 474/94 |
| 4,718,268 A | * | 1/1988 | Reid et al. .................. 73/19.01 |
| 5,027,643 A | | 7/1991 | Jenkins ........................ 73/23.39 |
| 5,032,721 A | | 7/1991 | Bacon et al. ................ 250/282 |
| 5,200,614 A | | 4/1993 | Jenkins ........................ 250/286 |
| 5,339,959 A | * | 8/1994 | Cornwell .................. 206/524.8 |
| 5,450,963 A | * | 9/1995 | Carson ..................... 206/524.8 |
| 5,491,337 A | | 2/1996 | Jenkins et al. .............. 250/287 |
| 5,818,059 A | * | 10/1998 | Coyne et al. ............. 250/507.1 |
| 5,859,362 A | * | 1/1999 | Neudorfl et al. ............. 73/23.2 |
| 5,931,189 A | * | 8/1999 | Sweeney et al. ........ 137/512.15 |
| 6,029,810 A | * | 2/2000 | Chen .......................... 206/287 |
| 6,202,849 B1 | * | 3/2001 | Graham .................... 206/524.8 |
| 6,499,574 B1 | * | 12/2002 | Anthony ....................... 190/36 |
| 2003/0047700 A1 | * | 3/2003 | Motonaka et al. ........ 251/149.1 |

OTHER PUBLICATIONS

VaporTracer[2] —Portable Explosives & Narcotics Detection and Indentification System, Ion Track Instruments, LLC, 2001.

* cited by examiner

Primary Examiner—Hezron Williams
Assistant Examiner—David Rogers
(74) Attorney, Agent, or Firm—Brian Lefort; Jones Day (57) ABSTRACT

The present invention is an interface between a piece of baggage and a preconcentrator. The baggage-preconcentrator interface is able be secured to the opening in the baggage, such as an opening created by a zipper. The baggage-preconcentrator interface provides a convenient entry point from which to extract air from the interior of baggage. The shape of such interface corresponds to that of the preconcentrator, which collects constituents of air. The preconcentrator is inserted into the baggage-preconcentrator interface and an air sample is extracted from the interior of the baggage and through both the interface and the preconcentrator. As the air is extracted, the constituents of air collect in the preconcentrator. After collecting the constituents, the preconcentrator is inserted into a testing unit capable of detecting trace amounts of explosives, such as an ion trap mobility spectrometer. The testing unit analyzes the constituents and determines whether any of them are explosive.

21 Claims, 10 Drawing Sheets

INTERFACE BETWEEN A PIECE OF BAGGAGE AND A PRECONCENTRATOR

CROSS-REFERENCE TO RELATED APPLICATIONS

This is related to application Ser. No. 10/224,688, entitled "Method of Analyzing the Constituents of Air Extracted from the Interior of a Piece of Baggage" filed contemporaneously herewith.

TECHNICAL FIELD

This invention relates to the field of testing for explosives and more particularly, using a testing unit capable of detecting trace amounts of explosives such as an ion trap mobility spectrometer to analyze the constituents of air extracted from the interior of a piece of baggage to determine whether the baggage contains explosives.

BACKGROUND

Aircraft, particularly those operated by passenger airlines, are considered terrorist targets. Thus, aviation security is essential to the safety of airline passengers. One attempt to minimize the possibility of a terrorist attack includes screening all baggage (i.e., luggage) that enters the aircraft. Specifically, both carry-on and checked baggage are screened for bombs and/or explosives.

Some of the current methods used to screen carry-on and checked baggage include manual inspection, X-ray, and trace detection. Manual inspection is invasive and often time consuming. Utilizing X-ray equipment is a non-invasive procedure. However, that method requires the operator of the X-ray equipment to promptly recognize the particular shape of the explosive device.

Figure 1:
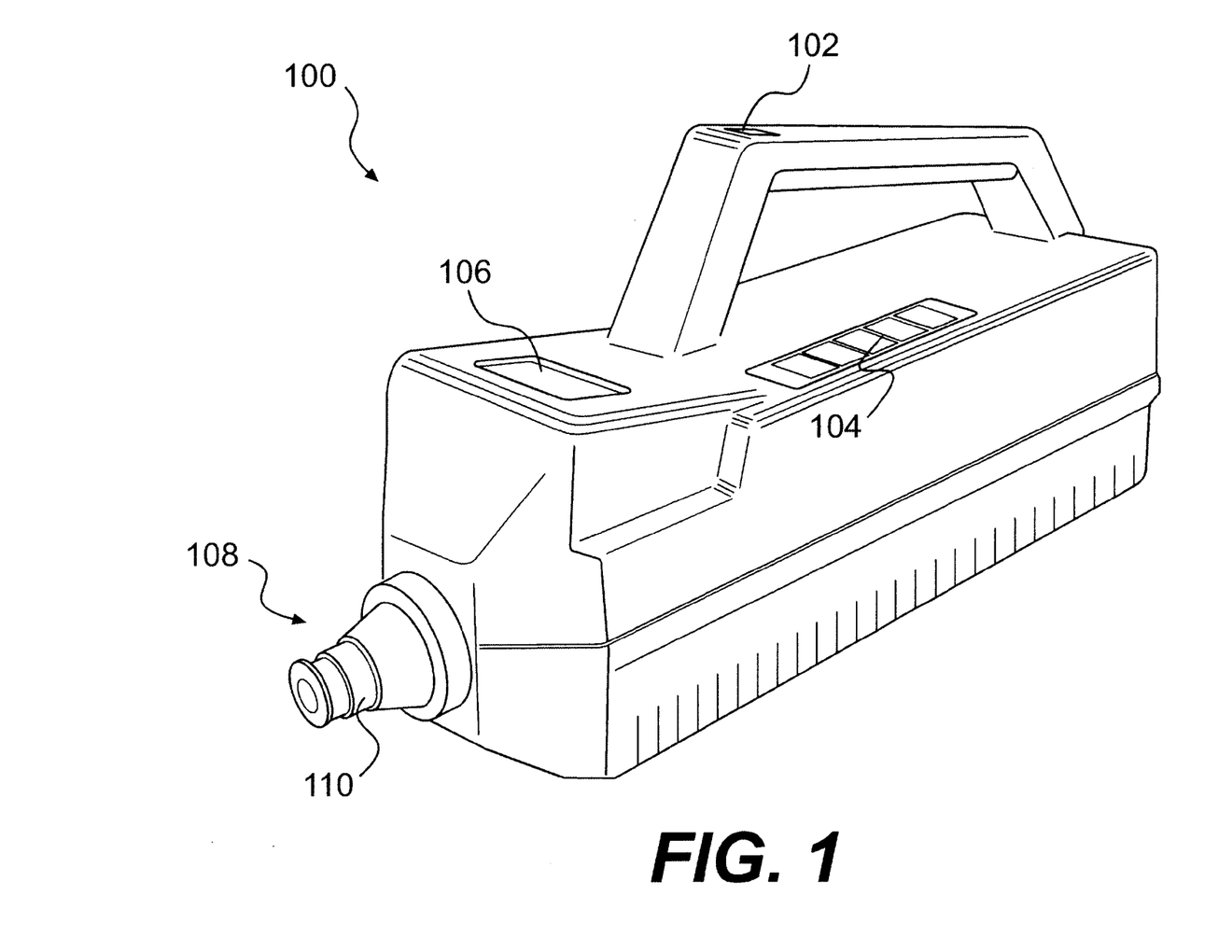
FIG. 1 is an illustration of an ion trap mobility spectrometer 100, which includes a start button 102, a control keypad 104, a LCD display 106 and a nozzle 108.

Trace detection is also less intrusive than manual inspection. One current trace detection technique includes swabbing the exterior of a piece of baggage and placing the swab in front of a testing unit capable of detecting trace amounts of explosives. One such testing unit is an ion trap mobility spectrometer, such as the VaporTracer$^2$® sold by Ion Track Instruments in Lowell, Mass. FIG. 1 illustrates a Vapor-Tracer$^2$® ion trap mobility spectrometer 100. That ion trap mobility spectrometer 100 includes a start button 102, a control keypad 104, a LCD display 106 and a nozzle 108.

Figure 2A:
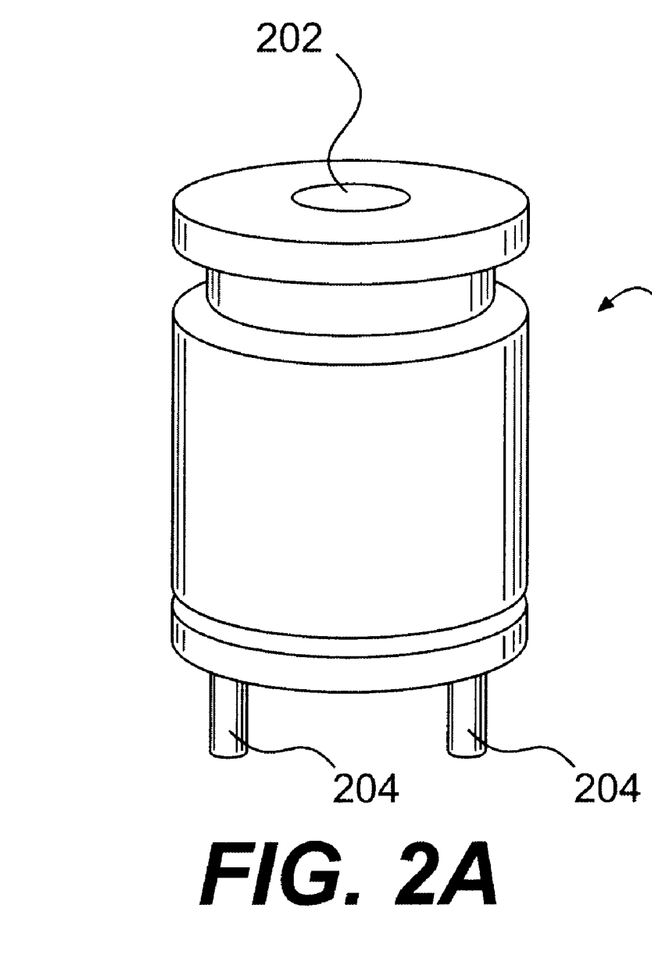
FIGS. 2A and 2B illustrate a preconcentrator 110 that can be included within the nozzle 108 of the ion trap mobility spectrometer 100 of FIG. 1.
Figure 2B:
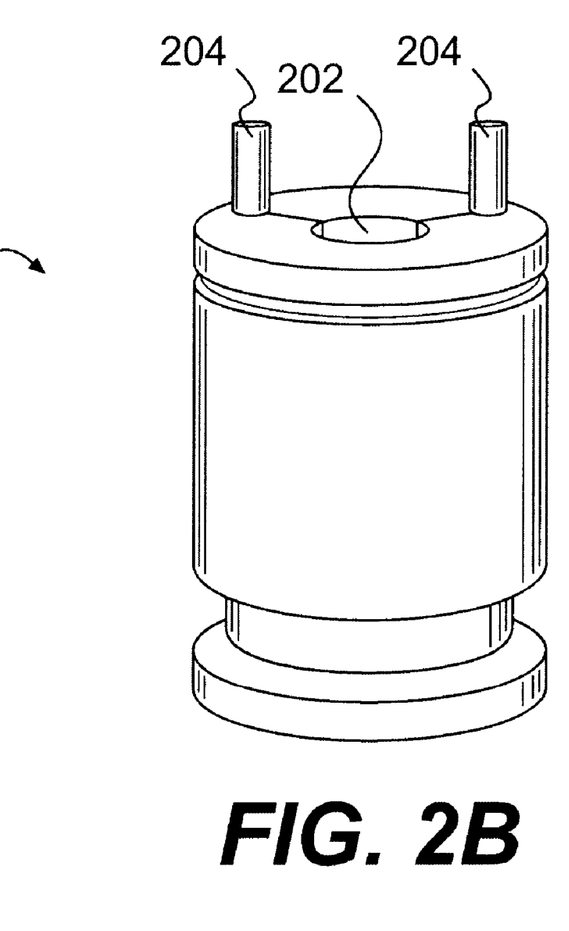

The nozzle 108 illustrated in FIG. 1 includes a preconcentrator 110. A more detailed illustration of one embodiment of a preconcentrator 110 is shown in FIGS. 2A and 2B. The preconcentrator 110 includes an orifice 202, a pair of electrodes 204 and a heating coil (not shown). The end of the preconcentrator 110 that includes the electrodes 204 is generally inserted into the ion trap mobility spectrometer 100. The orifice 202 allows air to pass from one end of the preconcentrator 110 to the other end.

For example, after the swab is passed over the exterior surface of the baggage, the swab is either placed in front of or rubbed onto the preconcentrator 110. The ion trap mobility spectrometer 100 includes a small vacuum unit (not shown) which draws the air and any constituents through the preconcentrator 110. For the purpose of this invention, the term "constituents" shall mean both particles in the air and vapor molecules. As the constituents pass through the preconcentrator 110, the heating coil volatizes the constituents, thereby creating vapors that can be detected by the ion trap mobility spectrometer 100. Accordingly, if the exterior of the bag includes trace amounts of explosives, the ion trap mobility spectrometer 100 will recognize the constituents as such.

Another possible trace detection technique includes placing the nozzle 102 of the ion trap mobility spectrometer 100 directly into the baggage and analyzing a sample of air within the baggage to determine whether the air contains explosive particles or vapors. However, placing the nozzle 102 directly into a piece of baggage and drawing an air sample therefrom is impractical and inefficient. Specifically, unless the entire ion trap mobility spectrometer 100 is placed within the baggage and the baggage is closed, the ion trap mobility spectrometer 100 will draw in a substantial amount of air from outside the baggage in addition to the air drawn from within the baggage, thereby obtaining a possibly erroneous sample and reading.

Furthermore, although the ion trap mobility spectrometer 100 includes a vacuum unit, the vacuum may not have enough capacity to effectively draw air from a normally sized piece of baggage. Moreover, the vacuum unit in the ion trap mobility spectrometer may not be large enough to efficiently screen multiple pieces of baggage. That is, depending upon the size of each piece of baggage, it may take several minutes for the ion trap mobility spectrometer to extract a sufficient volume of air from the baggage in order to produce an accurate reading. Assuming a single ion trap mobility spectrometer is used to screen several pieces of baggage, the overall efficiency for this technique would reduce even further. Moreover, not only must a sufficient volume of air be extracted from the baggage, but it is preferable to extract the air at a moderately high flow rate to produce an accurate reading. Thus, if the size of the baggage is relatively large, the vacuum unit included within the ion trap mobility spectrometer may be unable to extract an adequate volume of air at a rate sufficient to produce a meaningful test.

OBJECTS OF THE INVENTION

It is an object of the invention to determine whether explosives are contained within a piece of baggage.

It is another object of the invention to determine whether explosives are contained within a piece of baggage via sampling the air within the baggage.

It is another object of the invention to analyze the constituents of the air sample extracted from the interior of a piece of baggage.

It is a further object of the invention to analyze the constituents of the air sample extracted from the interior of a piece of baggage in a more efficient manner.

It is a further object of the invention to extract the air sample through the zipper of the baggage.

It is further object of the invention to collect the constituents of air in a preconcentrator from an ion mobility spectrometer.

It is even a further object of the invention to create an interface between the baggage and the preconcentrator.

SUMMARY OF THE INVENTION

The present invention is an interface between a piece of baggage and a preconcentrator. For the purposes of this invention, such an interface shall be referred to as a baggage-preconcentrator interface. The baggage-preconcentrator interface is able be secured to the opening in the baggage, such as an opening created by a zipper. After the baggage-preconcentrator interface is clamped to the teeth of the zipper and the zipper is closed, the preconcentrator is firmly and securely inserted into the baggage-preconcentrator interface because the shape of such interface matingly engages the preconcentrator. The baggage-preconcentrator interface, therefore, provides a securing mechanism through which an air sample may be extracted from the interior of the baggage and through the preconcentrator.

Accordingly, one embodiment of the baggage-preconcentrator interface includes a top securing member, a bottom securing member connected to said top securing member and forming a gap between it and the top securing member, and a recess corresponding to the exterior shape of a preconcentrator, wherein the recess comprises a vent that allows air to pass from the interior of the bag to the preconcentrator. It may also be preferable for the baggage-preconcentrator interface to include two clamps diametrically opposed from one another, wherein each of said clamps comprises bottom and top lips thereby creating a gap therebetween, and a lever connected to said top lip, thereby allowing the opening of the gap to be adjusted when the levers are squeezed and/or released.

The baggage-preconcentrator interface provides a convenient entry point from which to extract air from the interior of baggage. Moreover, the shape of such interface corresponds to that of the preconcentrator. Thus, an air sample passes through both the interface and the preconcentrator. Because the air sample passes through the preconcentrator, the constituents of air collect therein. Therefore, the baggage-preconcentrator interface of the present invention allows a truly representative sample of air and its constituents to be extracted from the interior of the bag. Assuming explosives reside in the baggage, the constituents of the air will include trace amounts of such explosives, which will collect in the preconcentrator as the air sample is extracted from the baggage. Thereafter, a testing unit capable of detecting trace amounts of explosives, such as an ion mobility spectrometer, can analyze the constituents collected in the preconcentrator and determine whether any of the constituents are explosive.

For example, the manner in which such a baggage-preconcentrator interface could be used in the process of analyzing the constituents of air within a piece of baggage is as follows: inserting a baggage-preconcentrator interface within a piece of baggage; inserting the preconcentrator into the recess of the baggage-preconcentrator interface; extracting air from the interior of the piece of baggage and through the vent in the baggage-preconcentrator interface and through the orifice in the preconcentrator, the preconcentrator collecting constituents of the air as the air passes therethrough; removing the preconcentrator from the baggage-preconcentrator interface; placing the preconcentrator into a testing unit capable of detecting a trace amount of an explosive; and analyzing the constituents by drawing the constituents from the preconcentrator into the testing unit and operating the testing unit to determine whether any of the constituents correspond to an explosive.

The foregoing features and advantages of the present invention will become more apparent in light of the following detailed description of exemplary embodiments thereof as illustrated in the accompanying drawings.

DESCRIPTION OF THE PREFERRED EMBODIMENTS

Figure 3:
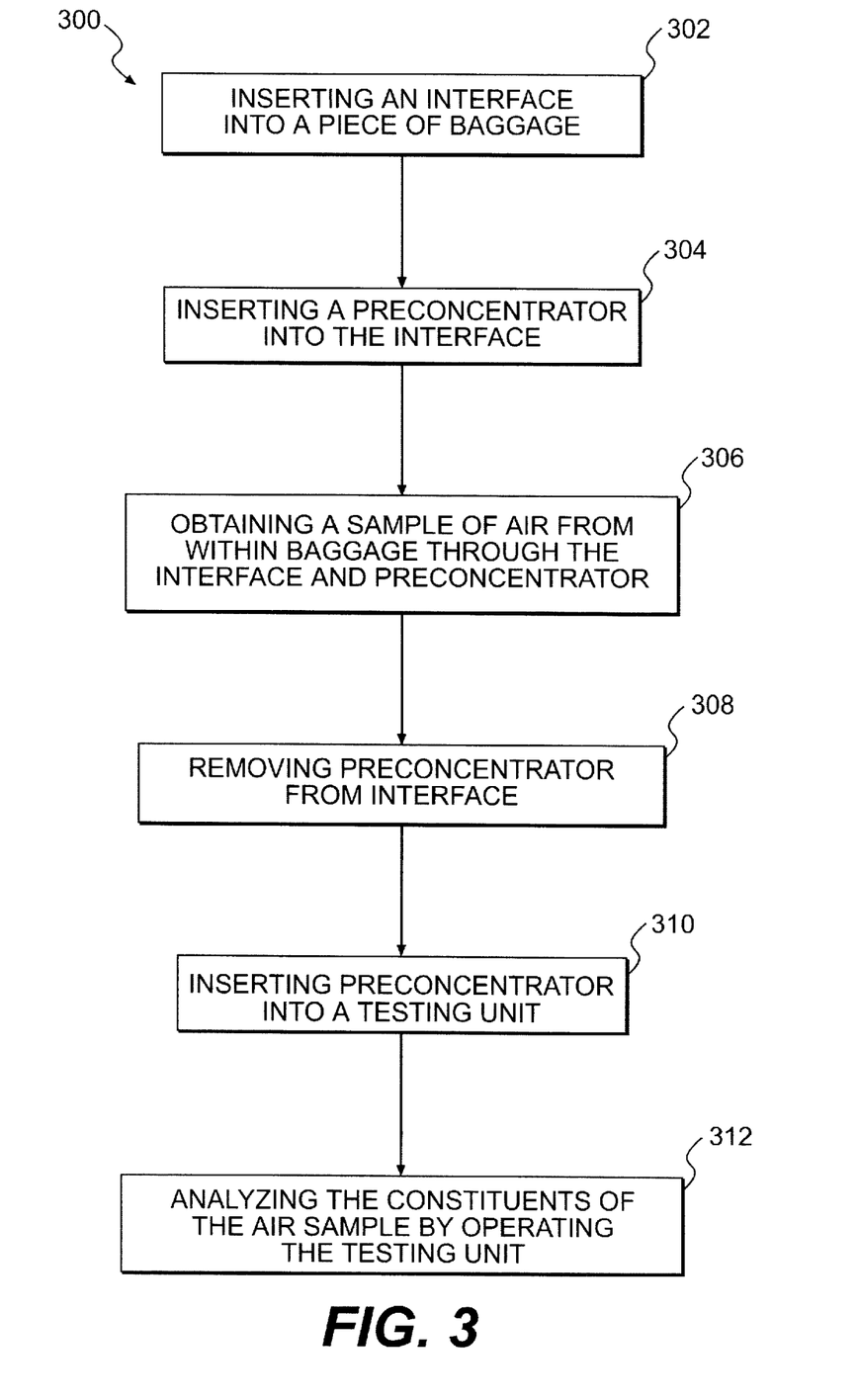
FIG. 3 is a flow diagram of one embodiment of the method of the present invention.

Referring to FIG. 3, there is shown a flow diagram of one embodiment of the method of the present invention. The method of the present invention is directed towards analyzing the air from the interior of a piece of baggage to determine whether explosives are included therein. Although the steps of the invention are listed in a particular order in FIG. 3 and explained in such order, it is not necessary that the invention be practiced in that exact order. Moreover, additional steps may be added to those illustrated in FIG. 3 and still be within the scope of the this invention.

The steps shown in FIG. 3 include: inserting a baggage-preconcentrator interface into a piece of baggage 302; inserting a preconcentrator into the baggage-preconcentrator interface 304; drawing a sample of air from within the baggage by vacuuming the air through the baggage-preconcentrator interface and the preconcentrator 306, thereby allowing the preconcentrator to collect constituents (i.e., particles or vapors) from such air; removing the preconcentrator from the baggage-preconcentrator interface 308; inserting the preconcentrator into a testing unit capable of detecting a trace amount of an explosive 310; and analyzing the constituents of the air sample by operating the testing unit 312.

Figure 4:
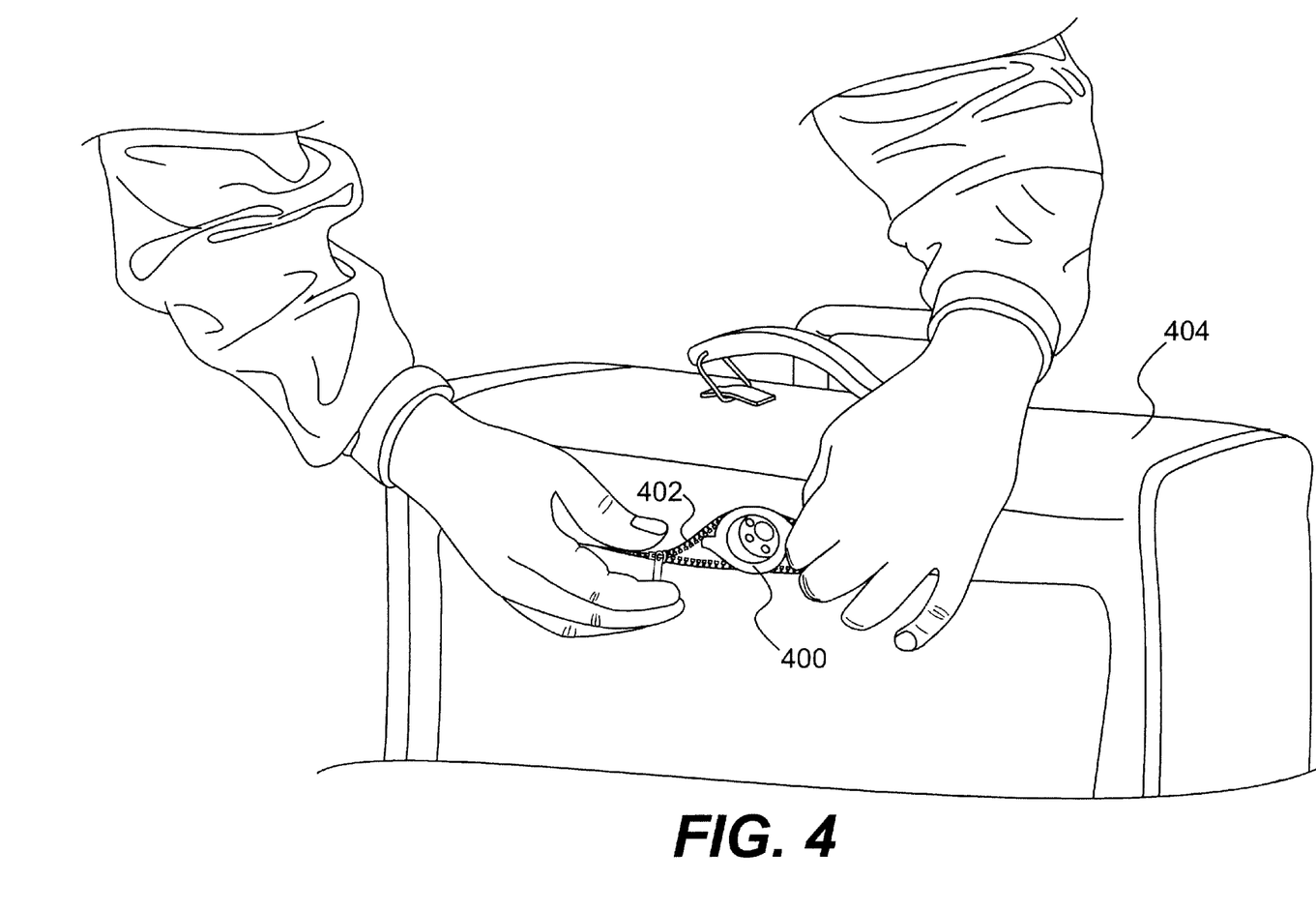
FIG. 4 illustrates a baggage-preconcentrator interface 400 being inserted into a piece of baggage 404 and particularly, into the zipper 402 of the baggage 404.
Figure 5A:
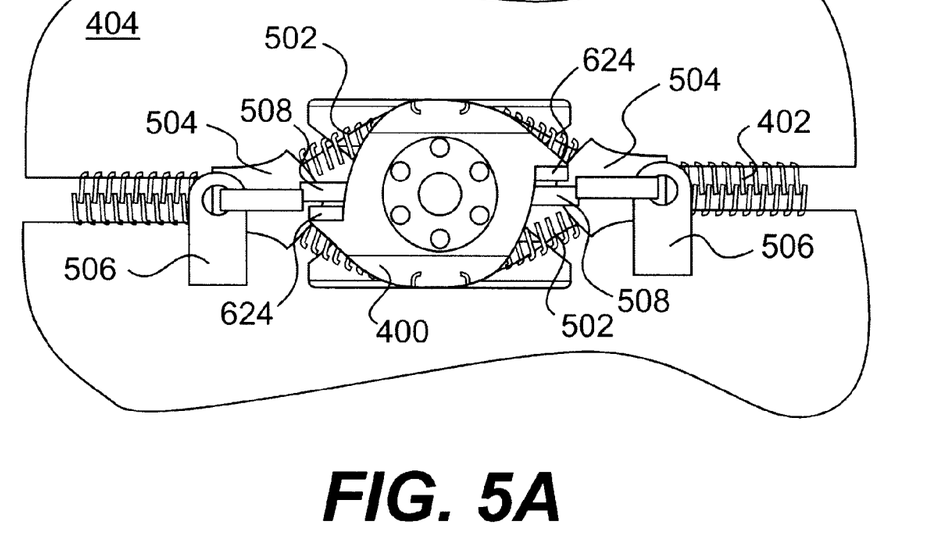
FIGS. 5A and 5B are enlarged views of the baggage-preconcentrator interface 400 inserted within the baggage's zipper 402 as seen in FIG. 4.
Figure 5B:
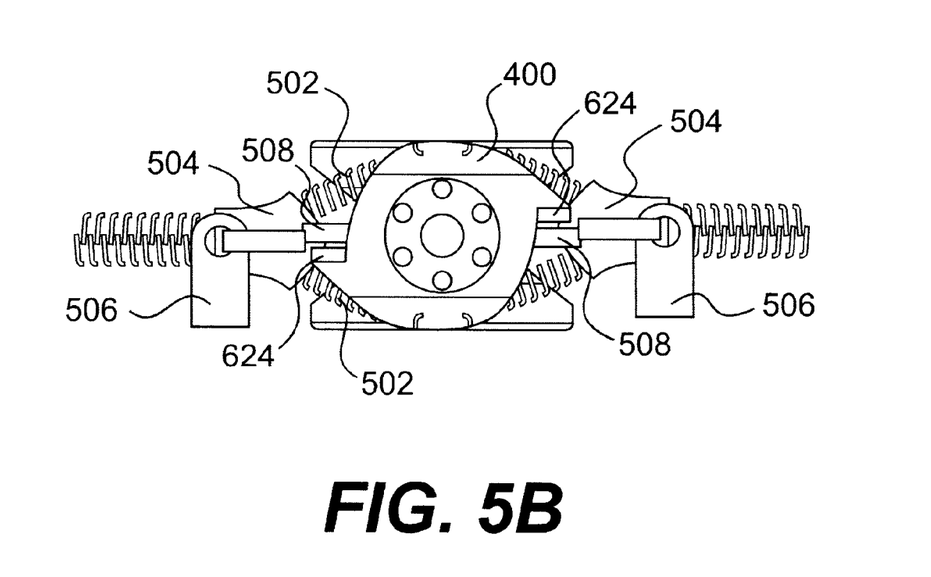

FIG. 4 illustrates one embodiment of step 302—the step of inserting a baggage-preconcentrator interface 400 into a piece of baggage 404. Specifically, FIG. 4 illustrates an individual inserting a baggage-preconcentrator interface 400 into the zipper 402 of a piece of baggage 404. FIGS. 5A and 5B are enlarged views of the baggage-preconcentrator interface 400 inserted within the zipper 402 of the baggage 404. Those figures illustrate that the zipper 402 includes two rows of teeth 502 and a two sliders 504, which further include pull tabs 506. And when the baggage-preconcentrator interface 400 is inserted into the zipper 402, the baggage-preconcentrator interface 400 grips at least a portion of each row of teeth 502.

Once the baggage-preconcentrator interface 400 is gripping the zipper's teeth 502, it may be preferable to close the zipper 402. Closing the zipper may include the step of sliding one or both of the sliders 504, via the pull tabs 506, toward the baggage-preconcentrator interface 400 until the slider(s) 504 is adjacent and/or abuts the baggage-preconcentrator interface 400. Some sliders 504 may include locking rings 508, which allow the sliders 504 to be locked together, thereby preventing someone from opening the zipper 402 without first removing a lock. As will be discussed below, it may be preferable for the baggage-preconcentrator interface 400 to include corresponding (i.e., complementary) locking rings 624. If the baggage-preconcentrator interface 400 includes locking rings 624, it may be desirable to slide the slider(s) 504 toward the baggage-preconcentrator interface 400 until the openings within the locking rings 508, 624 align with one another. Once the locking rings 508, 624 are aligned, it would be possible to secure the baggage-preconcentrator interface 400 to the sliders 504 by passing a lock or other type of fastening means through the holes within the locking rings 508, 624.

Figure 6:
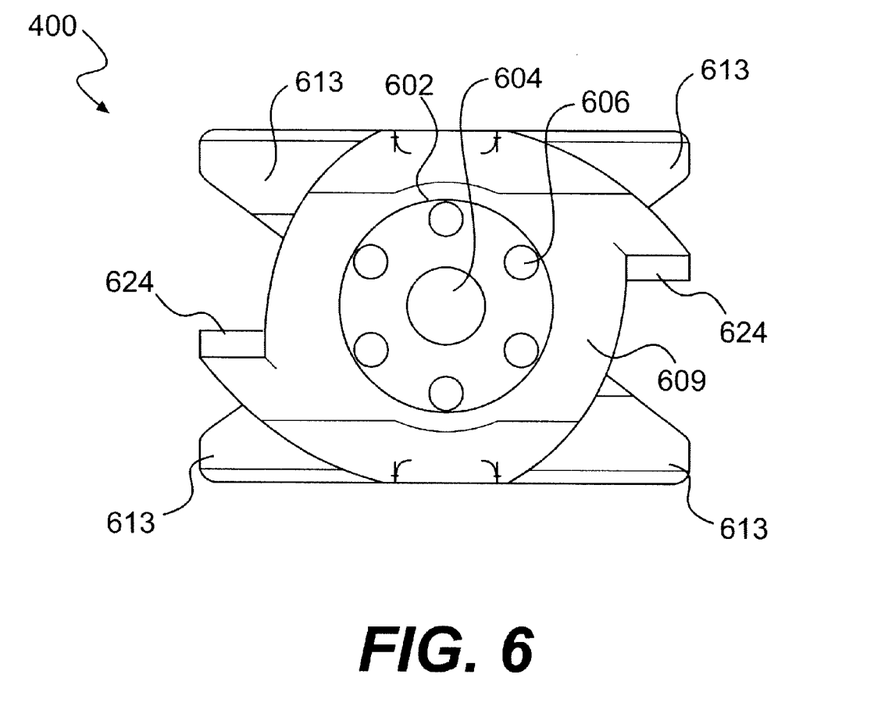
FIG. 6 is a top view of one embodiment of the baggage-preconcentrator interface 400 of the present invention.
Figure 7:
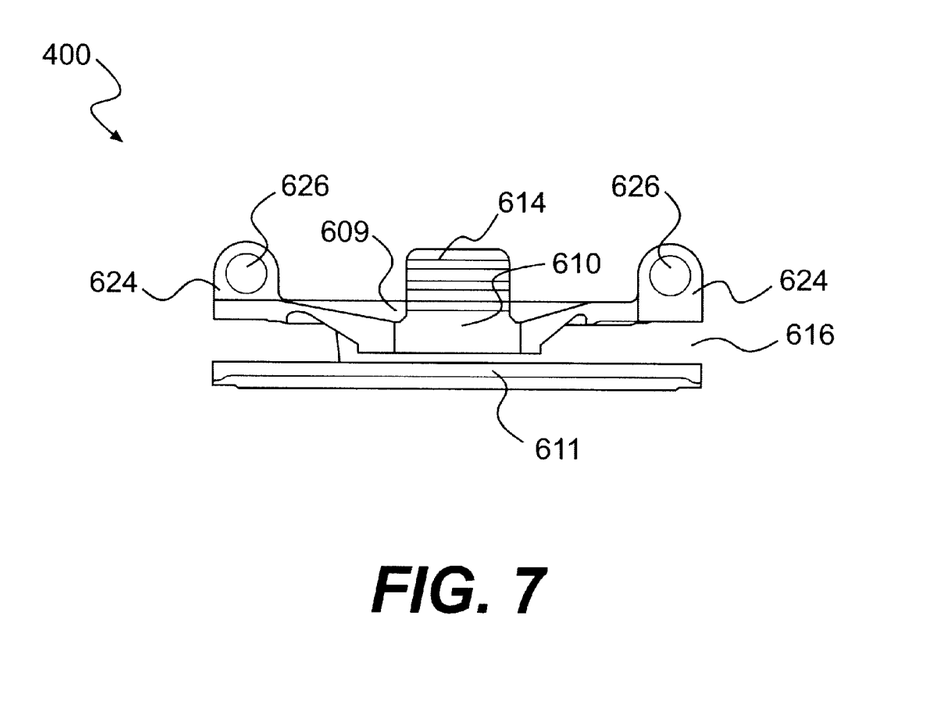
FIG. 7 is a side view of one embodiment of the baggage-preconcentrator interface 400 of the present invention.
Figure 8:
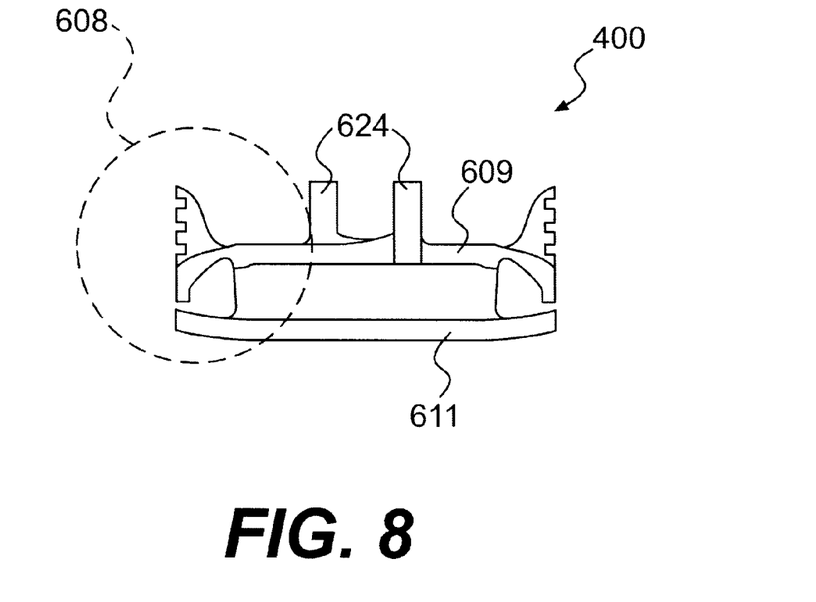
FIG. 8 is an end view of one embodiment of the baggage-preconcentrator interface 400 of the present invention, wherein such interface valve comprises means for gripping the zipper 402.

FIGS. 6 to 8 illustrate one embodiment of the baggage-preconcentrator interface 400 of the present invention. That embodiment includes a recess 602 and two clamps 608. The perimeter of the recess 602 has a shape that corresponds to the shape of the exterior of the preconcentrator 110. The preconcentrator 110 illustrated in FIGS. 2A and 2B has a cylindrical shape. Thus, the perimeter (i.e., circumference) of the preconcentrator 110 is circular. Because the shape of the perimeter of the recess 602 corresponds to the shape of the preconcentrator 110, the perimeter of the recess 602 is shown as circular. However, the present invention shall not be limited to using preconcentrators that have a circular exterior or cylindrical shape. Rather, the scope of this invention shall also apply to preconcentrators that have other shapes, such as any type of polygon or non-linear shape. What is important is that the perimetrical shape of the recess corresponds to the exterior shape of the preconcentrator such that when the preconcentrator is inserted into the recess, the recess matingly engages the preconcentrator and the two articles fit properly (i.e., firmly and securely) together.

Included within the recess 602 is a vent 604 that allows air to pass from one side of the baggage-preconcentrator interface 400 to the other. When the baggage-preconcentrator interface 400 is inserted within the baggage's zipper 402, the air within the baggage may pass through the baggage-preconcentrator interface 400 to the outside of the bag. Thus, the vent 604 provides a means for air to travel through the baggage-preconcentrator interface 400 and into the preconcentrator 110. Accordingly it is preferable that the vent 604 align with the orifice 202 of the preconcentrator 110

As illustrated in FIG. 2, the preconcentrator 110 may include electrodes 204. The baggage-preconcentrator interface 400, therefore, includes securing holes 606 to receive the electrodes 204 in the event the end of the preconcentrator 110 having the electrodes 204 is inserted into the recess 602. The shape and spacing of the securing holes 606, therefore, corresponds to the shape and spacing of the electrodes 204. Depending upon the orientation of the electrodes, however, the number of securing holes may differ from the number of electrodes. For example, the number of securing holes may be greater than the number of electrodes. The combination of the securing holes 606 and the electrodes 204 provides a means for securing the preconcentrator 110 to the baggage-preconcentrator interface 400. Such means prevents the preconcentrator 110 from rotating when it is in the recess 602 of the baggage-preconcentrator interface 400.

Figure 8A:
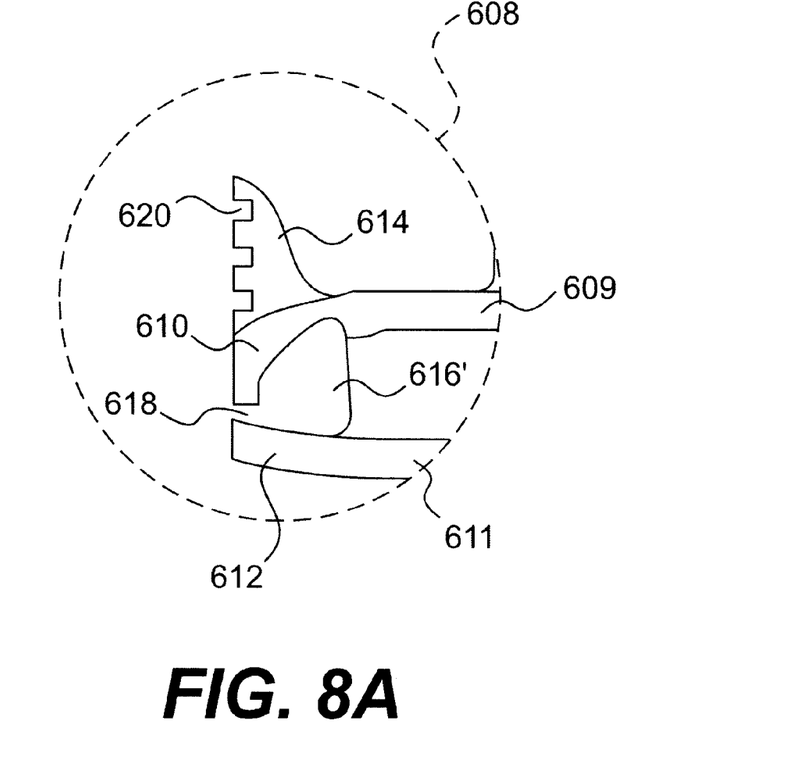
FIG. 8A is an enlarged view of the means for gripping the zipper 402.

Continuing to refer to FIGS. 6 to 8, including FIG. 8A, the baggage-preconcentrator interface 400 includes top and bottom securing members 609, 611 connected to one another The top and bottom securing members 609, 611 preferably have a circular shape when viewed from the top or the bottom of the baggage-preconcentrator interface 400. When the baggage-preconcentrator interface 400 is viewed from the side, a gap 616 exists between the top and bottom securing members 609, 611. Thus, when the baggage-preconcentrator interface 400 is inserted into the opening within the piece of baggage, the baggage-preconcentrator interface 400 can be turned (i.e., rotated), and as it turns, the baggage-preconcentrator interface 400 clasps the baggage. That is, when the baggage-preconcentrator interface 400 is inserted into the baggage, the baggage, and preferably the zipper, will be in the gap 616 between the top and bottom securing members 609, 611.

The top and bottom securing members 609, 611 provide the baggage-preconcentrator interface 400 means for gripping the opening of the baggage. Preferably, the baggage-preconcentrator interface 400 is inserted into the zipper 402 of a baggage 404 as shown in FIGS. 4 and 5. Thus, the top and bottom securing members 609, 611 provide the baggage-preconcentrator interface 40 with means for gripping a portion of each row of teeth 502 of the zipper 402.

It may also be preferable for the bottom securing member 611 to include wing portions 613 on one or both sides of the baggage-preconcentrator interface 400 As illustrated in FIGS. 5A and 5B, the wing portions 613 will be inside the baggage when the baggage-preconcentrator interface 400 is inserted into the baggage. The wing portions 613 provides the baggage-preconcentrator interface 400 with added stability when it is inserted into the baggage.

In an alternate embodiment of the present invention, it may be preferable for the baggage-preconcentrator interface 400 to include two clamps 608, which can provide additional means for gripping the opening of the baggage. As illustrated in FIG. 8A, the top securing member 609 may have a top lip portion 610, and the bottom securing member 611 may have a bottom lip portion 612. It is also preferable that the shape of the top lip 610 create a gap 616' between it and the bottom lip 612. Although it is not necessary, the gap 616' may also include an opening 618 such that the top and bottom lips 610, 612 closely approximate but do not contact one another. The shape of the gap 616' illustrated in FIG. 8A allows the clamps 608 of the baggage-preconcentrator interface 400 to grip the teeth of a zipper. However, the baggage-preconcentrator interface 400 may be inserted into another portion of the baggage. Accordingly, the shape of the gap and opening may change.

For example, the top and bottom lips 610, 612 may initially contact one another. Assuming the top and bottom lips 610, 612 initially contact one another, the baggage-preconcentrator interface 400 may need a means for opening the lips so that the baggage-preconcentrator interface 400 can be inserted into the baggage. Similarly, if the baggage-preconcentrator interface 400 has a gap and opening analogous to those illustrated in FIG. 8A, a means for enlarging the opening and/or gap may be needed in order to insert the baggage-preconcentrator interface 400 into the baggage. Thus, it may be preferable for the clamp 608 to include a lever 614 that is connected to the top lip 610, such that when the lever 614 is moved (i.e., pressed) toward the center of the baggage-preconcentrator interface 400, the size of the opening 618 will increase. Further assuming that the clamps 608 are diametrically opposed to one another, it may be preferable for the lever 614 to include grooves 620 (i.e., channels, serrations, etc.) so that an individual is able to have a firm grasp of the levers 614 when the individual simultaneously squeezes the levers 614 toward one another with his hand.

As mentioned above, some zippers include sliders 504 that have means for allowing a lock to secure (i.e., fasten) two sliders 504 together. Thus, it may be preferable for the baggage-preconcentrator interface 400 to include means for securing itself to two sliders 504 when such sliders abut the baggage-preconcentrator interface 400. One such means includes locking rings 624 connected to the baggage-preconcentrator interface 400. Each locking ring 624 includes an opening 626 that can be aligned with an opening in the baggage's locking ring 508. Upon placing a lock or some other fastening means through both the baggage-preconcentrator interface and baggage locking rings 508, 624, the baggage-preconcentrator interface 400 will be secured to the zipper's slider 504. Although it may be preferable for the baggage-preconcentrator interface 400 to have two locking rings 624, it may be sufficient to have only one locking ring 624.

The baggage-preconcentrator interface 400 may be constructed of many different types of materials. It is preferable that the baggage-preconcentrator interface 400 be somewhat flexible, yet firm. Thus, it may be preferable to construct the baggage-preconcentrator interface 400 from plastic(s), such as polypropylene. One such method of constructing the baggage-preconcentrator interface 400 from polypropylene is an injection molding process.

Figure 9:
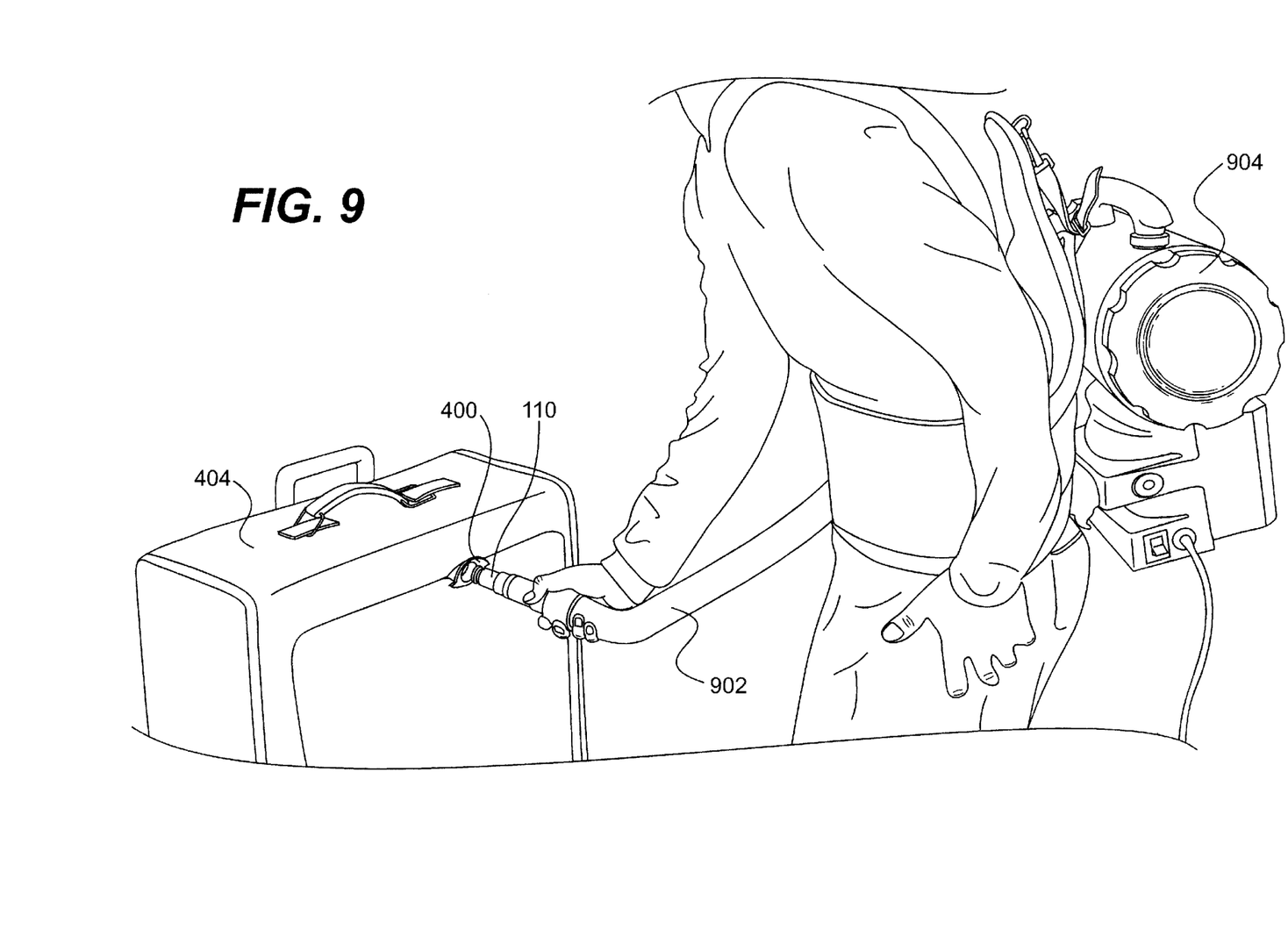
FIG. 9 illustrates the insertion of the preconcentrator 110 into the baggage-preconcentrator interface 400 and obtaining a sample of air within the baggage 404 by vacuuming the air through the baggage-preconcentrator interface 400 and preconcentrator 110.

After the baggage-preconcentrator interface 400 is securely inserted into the baggage 404, the preconcentrator 110 is inserted into the recess 602 of the baggage-preconcentrator interface 400. Thereafter, air is extracted from the interior of the piece of baggage 404 through the vent 604 in the baggage-preconcentrator interface 400 and through the orifice 202 in the preconcentrator 110 because the vent 604 and the orifice 202 align with one another when the preconcentrator 110 is inserted into the baggage-preconcentrator interface 400. One means for extracting air from inside of the baggage includes securing the preconcentrator 110 to one end of a hose 902, the other end of which is connected to a vacuum 904, as illustrated in FIG. 9.

When the vacuum 904 is turned "ON", a pressure differential across the preconcentrator 110 is created and air is extracted from the interior of the baggage 404 and through the preconcentrator 110. For a typically sized piece of baggage 404, it is preferable that the vacuum be rated to draw air at the rate of 100 to 3000 liters per minute. Depending upon the size of the baggage, it may even be more preferable to extract air from the baggage at the rate of 100 to 1000 liters per minute. It is also preferable that the vacuum draw the air sample through the preconcentrator 110 for about five (5) seconds. As the air passes through the preconcentrator 110, the constituents (i.e., particles and vapor molecules) in the air adhere to the interior of the preconcentrator 110. Specifically, the constituents adhere to the heating coil within the preconcentrator 110. Thus, the preconcentrator 110 is a means for collecting the constituents of the air. Although the preconcentrator 110 illustrated in FIG. 2 is designed to interact with a particular testing unit, the preconcentrator of the present invention shall include any type or shape of a constituent collector that operates with a testing unit capable of detecting trace amount of explosives.

Figure 10:
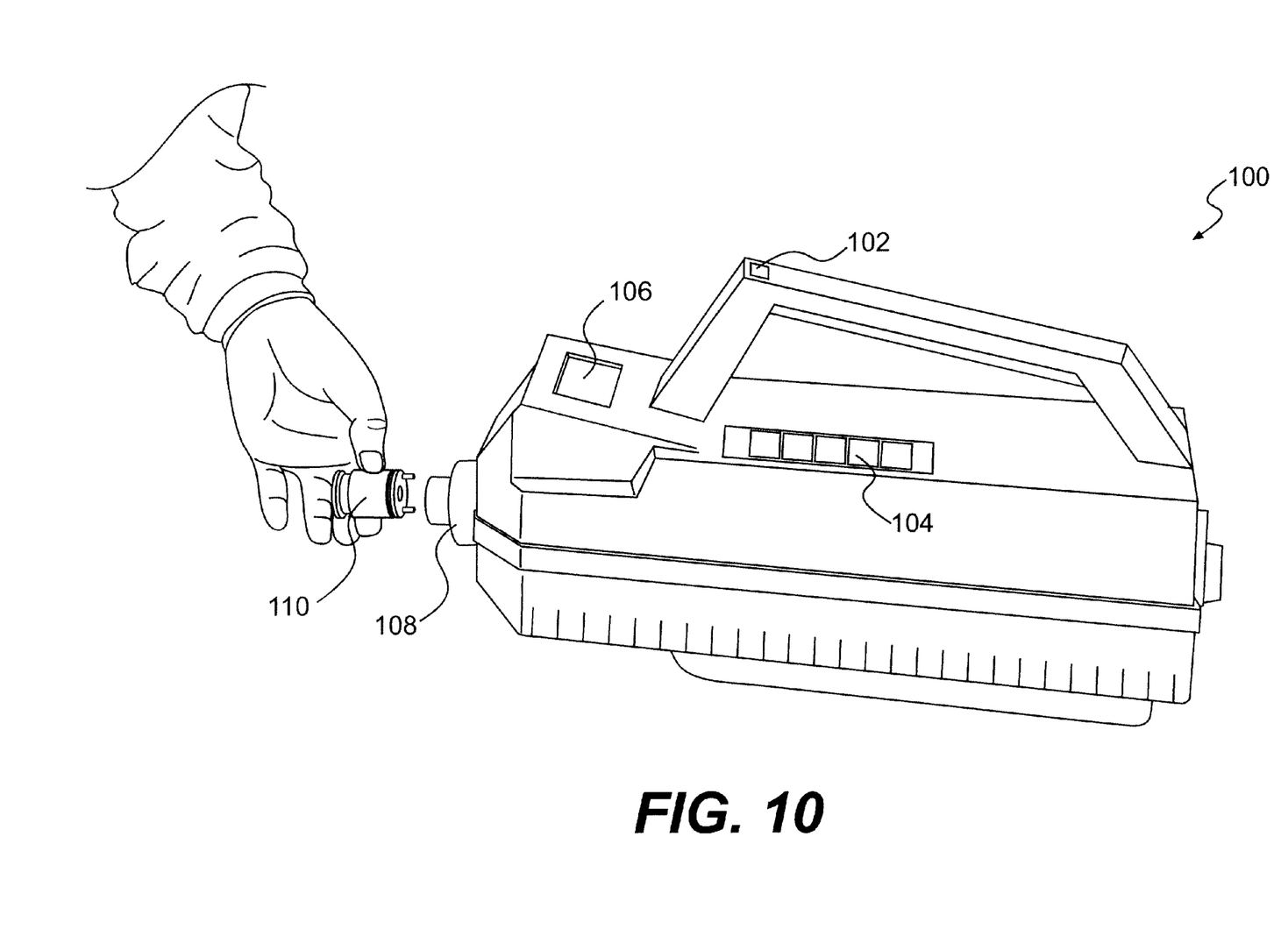
FIG. 10 illustrates the insertion of the preconcentrator 110 into the nozzle of the ion trap mobility spectrometer of FIG. 1.

Referring to FIG. 10, after extracting a sample of air through the preconcentrator 110, the preconcentrator 110 is inserted into a testing unit 100 capable of testing for trace amounts of explosives, such as a VaporTracer²® ion trap mobility spectrometer. It is preferred that the end of the preconcentrator 110 that has the electrodes 204 be inserted into the nozzle 108 of the ion trap mobility spectrometer. The electrodes transfer energy from the ion trap mobility spectrometer 100 to the preconcentrator 110, thereby activating the heating coil within the preconcentrator 110. As the temperature of heating coil increases, the constituents that collected on the heating coil begin to vaporize.

The VaporTracer²® ion trap mobility spectrometer includes a vacuum source (not shown). Thus, the vaporized constituents are drawn into the testing unit and analyzed. That is, the testing unit determines whether any of the vapors correspond to explosives. By inserting the preconcentrator 110 into a testing unit that has the capability to detect and analyze the constituents of air, such as the VaporTracer²® ion trap mobility spectrometer and operating that testing unit, an indication of whether the constituents explosive materials will be produced. Using the process outlined above, if the testing unit indicates the preconcentrator 110 includes explosive air-borne constituents, then the interior of the baggage may contain such explosives.

The process discussed above outlines drawing a sample of air through a preconcentrator and testing the preconcentrator after such air sample is extracted from one piece of baggage. However, a preconcentrator must be cleaned before it can be used again. Thus, assuming each airline passenger's baggage was checked using a separate preconcentrator, the total number of preconcentrators used to screen all of the carry-on and checked baggage for a single flight could be extraordinary. Therefore, it may be more efficient to screen groups of baggage using a single preconcentrator rather than screening each individual piece of baggage using a single preconcentrator.

For example, assuming a baggage-preconcentrator interface 400 was already inserted into a predetermined number (i.e., a group of five, ten, fifteen, or twenty bags), a single preconcentrator 110 could be inserted into a plurality of baggage-preconcentrator interfaces 400 corresponding to the predetermined number of baggage pieces. The method used to extract the series of air samples could include using the means illustrated in FIG. 9. Thereafter, the preconcentrator 110 could be inserted into the explosives testing unit, such as the VaporTracer²® ion trap mobility spectrometer, to determine whether any of the predetermined number of bags contain explosives. If the testing unit indicates the preconcentrator 110 contains explosive constituents, then that would indicate the presence of explosives within at least one of the pieces of baggage. Thereafter, all of the baggage within that group could be individually screened for explosives. Further screening methods could include using the method described above. That is, a separate preconcentrator would be used to screen each piece of baggage within the predetermined group, if the preconcentrator used to screen all of the pieces of baggage yielded a positive trace of an explosives Another method for individually screening each piece of baggage may include manual inspection or X-ray.

Figure 11:
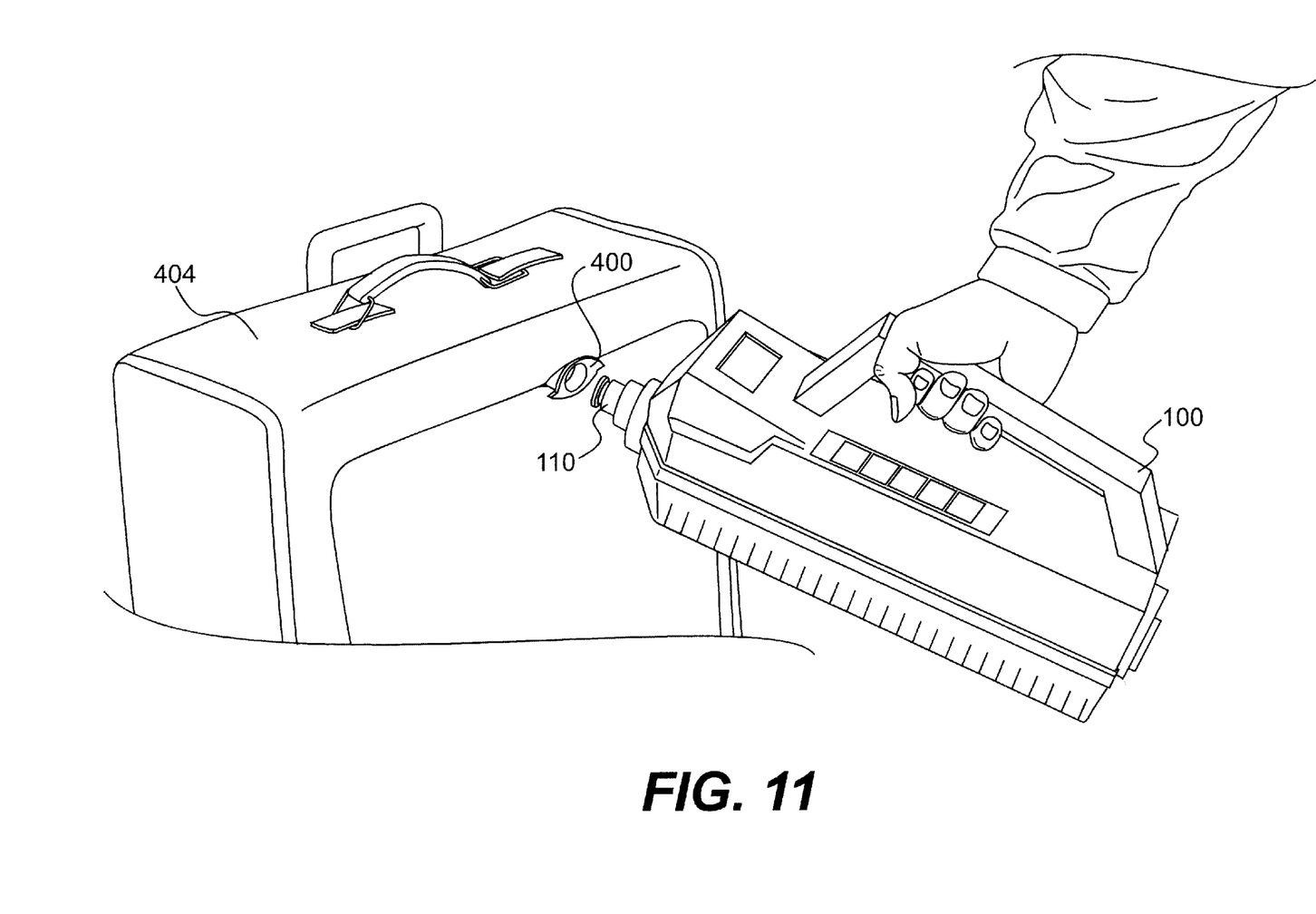
FIG. 11 illustrates the insertion of one end of the preconcentrator 110 into the baggage-preconcentrator interface 400 and the other end connected to the ion trap mobility spectrometer of FIG. 1.

An alternate embodiment of the method of the present invention is illustrated in FIG. 11. That is, rather than attaching the preconcentrator to the end of the hose and extracting air from the baggage through the preconcentrator using a separate vacuum unit as illustrated in FIG. 9 and thereafter inserting the preconcentrator into the testing unit as in FIG. 10, air may be extracted from the interior of the baggage and through the preconcentrator 110 while the preconcentrator 110 is attached to nozzle 108 of the testing unit 100. In order to extract air using this alternate embodiment, the testing unit 100 should include a vacuum unit that has sufficient capacity. Also, the duration that the preconcentrator 110 shall remain inserted in the baggage-preconcentrator interface 400 and air extracted there through shall be dependent upon the size of the vacuum unit.

Although the invention has been described and illustrated with respect to the exemplary embodiments thereof, it should be understood by those skilled in the art that the foregoing and various other changes, omissions and additions may be made without departing from the spirit and scope of the invention.

What is claimed is:

1. An interface between a preconcentrator and a piece of baggage, said interface comprising:
   (a) a top securing member;
   (b) a bottom securing member connected to said top securing member;
   (c) two clamps, wherein each of said clamps comprises a top lip connected to said top securing member and a bottom lip connected to said bottom securing member, thereby forming a gap therebetween; and
   (d) a recess having a perimetrical shape that corresponds to the perimetrical shape of the exterior of a preconcentrator, said recess comprising a vent.

2. The interface of claim 1 wherein the two clamps are diametrically opposed to one another.

3. The interface of claim 1 wherein the gap between said bottom and top lips creates an opening.

4. The interface of claim 2 wherein each of said clamps further comprises a lever connected to said top lip, thereby allowing the opening to expand and contract as said lever moves toward and away from the center of the interface, respectively.

5. The interface of claim 1 further comprising at least one securing hole within said recess.

6. The interface of claim 5 wherein said securing hole is complementary to an electrode of the preconcentrator.

7. An interface between a preconcentrator and a piece of baggage, said interface comprising:
   (a) a top securing member;
   (b) a bottom securing member connected to said top securing member and forming a gap therebetween;
   (c) a recess having a perimetrical shape that corresponds to the perimetrical shape of the exterior of a preconcentrator, said recess comprising a vent; and
   (d) a first locking ring.

8. The interface of claim 7 further comprising a second locking ring opposite said first locking ring.

9. An apparatus that serves as an interface between a preconcentrator and a zipper within a piece of baggage, wherein said zipper comprises two rows of teeth, said apparatus comprising:
   (a) means for receiving a preconcentrator;
   (b) means for air to travel through said receiving means; and
   (c) means for gripping a portion of each row of teeth of a zipper within a piece of baggage.

10. The apparatus of claim 9 further including means for securing at least one post of said preconcentrator to said apparatus.

11. The apparatus of claim 9 further comprising means for securing a lock for said baggage to said apparatus.

12. The apparatus of claim 9 wherein said gripping means comprises two clamps, wherein each of said clamps comprises:
   (i) a bottom lip;
   (ii) a top lip creating a gap between said bottom and top lips, wherein said gap comprises an opening; and
   (iii) means for enlarging said opening.

13. The interface of claim 12 wherein the two clamps are diametrically opposed to one another.

14. An interface between a preconcentrator and a piece of baggage, said interface comprising:
   (a) a recess having a perimetrical shape that corresponds to the perimetrical shape of the exterior of a preconcentrator, said recess comprising a vent; and
   (b) two clamps, wherein each of said clamps comprises a bottom lip and a top lip for gripping a portion of the baggage.

15. The interface of claim 14 wherein the two clamps are diametrically opposed to one another.

16. The interface of claim 14 wherein the gap between said bottom and top lips creates an opening.

17. The interface of claim 14 wherein each of said clamps further comprises a lever connected to said top lip, thereby allowing the opening to expand and contract as said lever moves toward and away from the center of the interface, respectively.

18. The interface of claim 14 further comprising at least one securing hole within said recess.

19. The interface of claim 18 wherein said securing hole is complementary to an electrode of the preconcentrator.

20. The interface of claim 14 further comprising a first locking ring.

21. The interface of claim 20 further comprising a second locking ring opposite said first locking ring.

* * * * *